United States Patent [19]

Onoda et al.

[11] 4,071,568

[45] Jan. 31, 1978

[54] PROCESS FOR PRODUCING GLYCOL MONOETHER

[75] Inventors: Takeru Onoda, Yokohama; Shimpei Tomita, Kurashiki, both of Japan

[73] Assignee: Mitsubishi Chemical Industries Limited, Tokyo, Japan

[21] Appl. No.: 745,927

[22] Filed: Nov. 29, 1976

[30] Foreign Application Priority Data

Dec. 12, 1975 Japan .................. 50-148002
Dec. 17, 1975 Japan .................. 50-150386

[51] Int. Cl.$^2$ .................. C07C 41/00; C07C 41/10
[52] U.S. Cl. .................. 260/615 R; 260/611 R; 260/611 A; 260/613 R; 260/613 D
[58] Field of Search ........... 260/611 R, 611 A, 613 R, 260/613 D, 615 R

[56] References Cited

U.S. PATENT DOCUMENTS

| 2,555,950 | 6/1951 | Wilson | 260/615 R |
|---|---|---|---|
| 2,623,906 | 12/1952 | Gresham | 260/615 R |
| 3,239,569 | 3/1966 | Slaugh et al. | 260/604 HF |
| 3,274,263 | 9/1966 | Greene et al. | 260/604 HF X |
| 3,278,612 | 10/1966 | Greene | 260/604 HF |
| 3,290,379 | 12/1966 | Eisenmann | 260/604 HF |
| 3,310,576 | 3/1967 | Mertzweiller et al. | 260/604 HF X |
| 3,547,964 | 12/1970 | Olivier | 260/604 HF X |
| 3,594,425 | 7/1971 | Brader et al. | 260/604 HF |
| 3,627,843 | 12/1971 | Pregaglia et al. | 260/604 HF |
| 3,839,471 | 10/1974 | Wilkes | 260/604 HF X |
| 3,857,893 | 12/1974 | Nozaki | 260/604 HF |
| 3,931,332 | 1/1976 | Wilkes | 260/604 HF |

FOREIGN PATENT DOCUMENTS

| 875,802 | 5/1953 | Germany | 260/615 R |
|---|---|---|---|
| 890,945 | 10/1953 | Germany | 260/615 R |

*Primary Examiner*—Howard T. Mars
*Attorney, Agent, or Firm*—Bierman & Bierman

[57] ABSTRACT

Glycol monoethers are produced in high yields by reacting an acetal with carbon monoxide and hydrogen in the presence of a catalyst comprising a cobalt compound and a trivalent organic phosphorus compound or a bidentate chelate ligand containing nitrogen or oxygen. An aldehyde or a compound capable or releasing an aldehyde under reaction conditions and an alcohol can be used instead of the acetal.

19 Claims, No Drawings

PROCESS FOR PRODUCING GLYCOL MONOETHER

This application claims the priority of Japanese applications 7 Nos. 148002/75 filed Dec. 12, 1975 and 150386/75 filed Dec. 17, 1975.

BACKGROUND OF THE INVENTION

This invention relates to a process for producing a glycol monoether by reacting an acetal or by reacting aldehyde and alcohol with carbon monoxide and hydrogen in the presence of a novel catalyst.

Glycol monoethers have a wide variety of applications as solvents and reaction media. In the prior art, glycol monoethers are commercially produced by preparing an olefin oxide from an olefin and adding a suitable alcohol thereto. Such conventional methods use an olefin, which is a petroleum product, as the starting material. The recent problems of cost and supply by the petroleum chemical industry has caused reconsideration of these methods of production, and research has been carried out seeking a new method of producing glycol monoethers from a starting material other than an olefin.

Among these new methods is the reaction of an acetal with carbon monoxide and hydrogen in the presence of a cobalt carbonyl catalyst (West German Pat. Nos. 875,802 and 890,945). This method, however, suffers from the disadvantage of low selectivity of the glycol monoether. In addition, since the cobalt carbonyl is inevitably decomposed when the glycol monoether is separated from the reaction product by distillation, the catalyst cannot be recycled.

It has been found that cobalt carbonyl combined with a trivalent organic phosphorus compound such as tertiary phosphine or a bidentate chelate ligand containing nitrogen or oxygen can improve the selectivity of the glycol monoether to a considerable extent. In addition, such a combination can stabilize the catalyst so that it can be recycled without complicated catalyst recovery and regeneration. This is possible because no decomposition takes place during separation of the glycol monoether from the reaction product by distillation.

SUMMARY OF THE INVENTION

An object of this invention is to provide a process for producing a glycol monoether that is commercially advantageous.

Another object of this invention is to provide a process for producing a glycol monoether by the use of a stabilized catalyst.

A further object of this invention is to provide a process for producing a glycol monoether in high yields.

According to this invention, these objects are attained by reacting (A) at least one member selected from the group consisting of (i) an acetal, (ii) an aldehyde and an alcohol, and (iii) a compound capable of releasing an aldehyde under reaction conditions and an alcohol with (B) carbon monoxide and (C) hydrogen in the presence of a catalyst comprising (1) a cobalt compound and (2) at least one compound selected from the group consisting of a trivalent organic phosphorus compound, a bidentate chelate ligand containing nitrogen and a bidentate chelate ligand containing oxygen.

DETAILED DESCRIPTION OF THE PREFERRED EMBODIMENTS

The acetal employed as a starting material in this invention may be an acetal having the general formula:

$$R^1OCHR^3OR^2$$

wherein $R^1$ and $R^2$ are the same or different and represent aliphatic or alicyclic hydrocarbon radicals of 1 to 8 carbon atoms or aromatic hydrocarbon radicals of 6 to 7 carbon atoms; and $R^3$ represents hydrogen, an aliphatic or alicyclic hydrocarbon radical of 1 to 8 carbon atoms or an aromatic hydrocarbon radical of 6 to 7 carbon atoms. The hydrocarbon radicals may have a substituent inert to the reaction. Typical of the acetal compounds used are formaldehyde dialkyl acetals having an alkyl group of 1 to 8 carbon atoms, such as formaldehyde dimethyl acetal, formaldehyde dibutyl acetal, acetaldehyde dialkyl acetals having an alkyl group of 1 to 8 carbon atoms, such as acetaldehyde diethyl acetal and the like.

According to the present invention, a commercially important ethylene glycol monoether can be produced from an acetal of formaldehyde as shown by the following reaction formula.

$$CH_2(OR)_2 + 2H_2 + CO \rightarrow ROCH_2CH_2OH + ROH$$

Other ethers including $ROCH_3$, $ROCH_2CH_2OR$, $ROCH_2CH_2OCH_2CH_2OH$, $ROCH_2CH(OR)CH_2OH$, etc. are also formed as by-products. In the formulae, R represents the same radical as $R^1$ or $R^2$ in the general formula (1).

Instead of using an acetal, an aldehyde (or a compound capable of releasing an aldehyde under reaction conditions) and an alcohol can be used as the starting materials. The aldehyde and the alcohol which may be employed in this invention have the following general formulae, respectively:

$$R^3CHO \qquad (2)$$

$$R^4OH \qquad (3)$$

In the formulae, $R^3$ is as defined in the formula (1) and $R^4$ is the same radical as $R^1$ or $R^2$ in the formula (1). Typical of the aldehyde compounds that can be used are aliphatic aldehydes such as formaldehyde and acetaldehyde. Typical of the alcohols that can be used are saturated aliphatic alcohols such as ethyl alcohol and butyl alcohol. Examples of the compound capable of releasing an aldehyde under reaction are aldehyde polymers such as paraformaldehyde and trioxane. When an aldehyde and an alcohol are used instead of the acetal, the ratio of alcohol to aldehyde is not critical, but is usually in the range of 0.01 to 100 moles of alcohol per mole of aldehyde, preferably in the range of 0.1 to 50 moles of alcohol per mole of the aldehyde.

Further, the ratio of carbon monoxide to hydrogen is not critical. For the sake of increasing the rate of reaction, 0.1 to 10 moles of hydrogen per mole of carbon monoxide may preferably be used. A gaseous mixture of carbon monoxide and hydrogen may further contain an inert gas such as methane, argon or nitrogen.

According to this invention, the reaction proceeds in the presence of a catalyst comprising (1) a cobalt compound and (2) a trivalent organic phosphorus compound or a bidentate chelate ligand containing nitrogen or oxygen. The cobalt compound employed herein may be cobalt carbonyl or compounds capable of forming cobalt carbonyl under reaction conditions. It is believed that the cobalt compound and the phosphorus compound or chelate ligand containing nitrogen or oxygen are so combined that a complex of cobalt coordinated with carbon monoxide and the phosphorus compound or the chelate ligand is formed under reaction conditions. The catalyst may be introduced into a reaction system in either of the following ways. First, the cobalt compound is combined with the phosphorus compound or the chelate ligand to form a complex thereof which is then introduced into the reaction system. Alternatively, the phosphorus compound or chelate ligand and the cobalt compound are separately introduced into the reaction system so that they form a complex under the reaction conditions. Illustrative of the complexes which can be prepared prior to introduction into the reaction system are $HCo(CO)_3(R'_3P)$, $Co_2(CO)_6(R'_3P)_2$ and other complexes can be prepared by conventional techniques. In the formulae, R' represents a radical bonded to a phosphorus atom in a phosphorus compound as described hereinafter.

If the phosphorus compound or chelate ligand and the cobalt compound are separately introduced into the reaction system, dicobalt octacarbonyl is typical of the cobalt compounds used. Cobalt compounds capable of forming cobalt carbonyl under reaction conditions may also be used; for example, cobalt oxide, organic acid salts of cobalt such as cobalt acetate and cobalt laurate, and inorganic acid salts of cobalt such as cobalt nitrate, cobalt sulfate and cobalt halides.

The trivalent organic phosphorus compound which may be employed in combination with the cobalt compound includes tertiary phosphines and phosphites. Examples of the tertiary phosphines are phosphines having alkyl group of 1 to 8 carbon atoms, such as tributyl phosphine, trioctyl phosphine, triisopropyl phosphine, etc.; phosphines having aryl group of 6 to 7 carbon atoms such as triphenyl phosphine, tritolyl phosphine, etc.; and cycloalkyl phosphines such as tricyclohexyl phosphine, etc. Other phosphines having two or more phosphorus atoms such as bis(diphenyl phosphino)methane, bis(diphenyl phosphino)ethane, bis(diphenyl phosphino)propane, etc. are preferred because they function as chelate ligands and generally afford higher yields. Examples of the tertiary phosphites are phosphites corresponding to the above-mentioned phosphines such as triphenyl phosphite, tributyl phosphite, etc.

It is to be noted that instead of the phosphorus compound, the corresponding trivalent arsenic or antimony compounds such as triphenyl arsine and triphenyl stibine may also be used, but are less preferred than the phosphorus compounds.

The nitrogen-containing bidentate chelate ligands useful in this invention include diamines such as

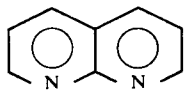

and $Me_2NCH_2CH_2NME_2$ (Me means methyl group), and dinitrils such as $NC(CH_2)_nCN$ ($n = 1$–$10$) and

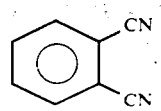

The oxygen-containing bidentate chelate ligands include diketones such as $CH_3COCH_2COCH_3$, diesters such as $EtOCOCH_2COOEt$ (Et means ethyl group), bisphosphine dioxides such as $Ph_2P(O)CH_2CH_2P(O)Ph_2$ (Ph means phenyl group), and the like.

Among the preferred compounds which are employed together with the cobalt compound to form a complex catalyst, are trivalent organic phosphorus, especially those having two or more phosphorus atoms and functioning as a chelate ligand.

The phosphorus and cobalt compounds are used in such amounts that the atomic ratio of phosphorus to cobalt is 0.1 to 100. Under equivalent reaction conditions, a larger proportion of phosphorus requires a higher pressure because of a decreased rate of reaction. Further, proportion of phosphorus that is too small will result in a less stable catalyst. Bearing in mind these factors, the atomic ratio of phosphorus to cobalt is preferably in the range of 0.3 to 10.

The chelate ligand is used in an amount such that the number of gram moles of the bidentate chelate ligand per gram atom of cobalt is generally in the range of 0.1 to 100, preferably from 0.3 to 50. The ratio varies widely depending upon whether the coordinating atom is nitrogen or oxygen.

The amount of the catalyst to be used varies depending upon the kinds of catalyst components, the kinds of the starting material and the reaction conditions. The amount used is generally in the range of $10^{-1}$ to $10^{-5}$ gram atom of cobalt the per gram mole of the acetal or aldehyde. A smaller amount of the catalyst below the lower limit may be used because the reaction will take place satisfactorialy but will require an extended period of time. On the other hand, a larger amount of the catalyst does not interfere with the reaction.

The reaction of the present invention can proceed in the absence of a solvent. It may also proceed in the presence of an inert solvent. Specific examples of the solvents used are ethers such as diethyl ether, dioxane, diphenyl ether, etc.; esters such as methyl acetate, methyl formate, etc.; ketones such as acetone, diethyl ketone, etc.; aromatic hydrocarbons such as benzene, toluene, etc.; aliphatic hydrocarbons such as hexane, heptane, etc.; alcohols such as methanol, butanol. If an alcohol is used as the solvent, it is preferable to use the alcohol which is a constituent of the acetal. The solvent preferably has a higher boiling point than the glycol monoether resulting from the reaction because such a solvent is particularly suitable for recycling the catalyst. However, in the case of a low boiling solvent, the catalyst may be recycled by accumulating products having a high boiling point or by leaving in part of the glycol monoether produced.

The method of this invention may advantageously be carried out either in batchwise or in a continuous manner. Generally, the reaction is carried out under pressure. Preferably the pressure is from 10 to 1,000 $K_9/cm^2$ gauge. The reaction temperature is usually 50° to 300° C, preferably 100° to 250° C. After the reaction is completed, the resulting glycol monoether may be easily separated by conventional techniques; for example, by distillation. The catalyst used in this invention remains dissolved in the distillation residue even after the distillation of the reaction mixture is completed and can be recycled without complicated catalyst recovery and regeneration. This invention permits the selective production of glycol monoethers from acetals or from aldehyde and alcohol and the recycling of the catalyst dissolved in the reaction medium. In order to enable those skilled in the art to easily practice the present invention, the following examples are set forth for purposes of illustration and are not intended to limit the scope thereof.

In all the following examples and comparative examples, a 200-ml stainless steel autoclave equipped with a magnetic stirrer is used as a reactor. Abbreviations Et, Bu, and Ph (or $\phi$) stand for ethyl, butyl, and phenyl, respectively.

EXAMPLES 1–7 AND COMPARATIVE EXAMPLE 1

A reactor is charged with 16 g (0.1 mole) of formaldehyde di-n-butyl acetal [$CH_2(O-n-Bu)_2$], 0.682 g (2.0 mmoles) of dicobalt octacarbonyl [$Co_2(CO)_8$], 2.0 mmoles of one of the trivalent organic phosphorus compounds listed in Table 1, and 33 ml of toluene. After the atmosphere in the reactor is replaced with argon, carbon monoxide is added under pressure until a predetermined level is reached. The temperature is then raised to 160° C. Thereafter, hydrogen is added under pressure until a predetermined level is reached and the reaction is initiated and continued until further absorption of gas is observed. The reaction product is analyzed by gas chromatography. The yields of butyl cellosolve [$n-BuOCH_2CH_2OH$] obtained based on the amount starting acetal used are shown in Table 1.

until there is no further absorption of gas. The reaction product is analyzed by gas chromatography.

Analysis shows that 0.0422 mole of propylene glycol $\beta$-monoethyl ether [$CH_3CH(OEt)CH_2OH$] is produced (yield 42.4%).

EXAMPLE 9

Example 8 is repeated except that formaldehyde diisobutyl acetal [$CH_2(O-i-Bu)_2$] is used as the acetal and the reaction time is 8 hours.

Analysis shows that 0.0556 mole of isobutyl cellosolve [$i-BuOCH_2CH_2OH$] is produced (yield 55.6%).

EXAMPLE 10

A reactor is charged with 3 g of paraformaldehyde (corresponding to 0.1 mole of formaldehyde), 46 ml (about 0.5 mole) of n-butanol [$n-BuOH$], 2.0 mmoles of dicobalt octacarbonyl [$Co_2(CO)_8$], and 2.0 mmoles of tri-n-butyl phosphine [$Bu_3P$]. The atmosphere in the reactor is replaced with argon and a gas mixture having a molar ratio of $H_2/CO$ of 1.6 is then introduced under pressure until a pressure of 180 kg/cm² gauge is reached in the reactor. The temperature is then increased to 160° C and the reaction is carried out for 3 hours until there is no more absorption of gas.

Analysis shows that 0.051 mole of butyl cellosolve [$n-BuOCH_2CH_2OH$] is produced (yield 51%).

COMPARATIVE EXAMPLE 2

Example 10 is repeated except that tri-n-butyl phosphine is not added. Analysis shows that butyl cellosolve is produced in a yield of 42%.

EXAMPLE 11

A reactor is charged with 0.1 mole of formaldehyde

Table 1

| | Trivalent organic phosphorus compound | Total pressure* (kg/cm² gauge) | Ratio of $H_2/CO$* | Reaction time (hr) | Yield of n-$BuOCH_2CH_2OH$ (%) |
|---|---|---|---|---|---|
| Example 1 | $(C_8H_{17})_3P$ | 225 | 2/1 | 6 | 67.1 |
| Example 2 | $n-Bu_3P$ | 236 | 2/1 | 5 | 67.4 |
| Example 3 | $Et_2NPBu_2$ | 225 | 2/1 | 4 | 67.1 |
| Example 4 | $\phi_2PCH_2P\phi_2$ | 225 | 2/1 | 5 | 70.9 |
| Example 5 | $\phi_2P(CH_2)_2P\phi_2$ | 220 | 2/1 | 5 | 70.6 |
| Example 6 | $\phi_2P(CH_2)_2P\phi_2$ | 235 | 4/1 | 8 | 74.4 |
| Example 7 | $\phi_2P(CH_2)_3P\phi_2$ | 235 | 2/1 | 10 | 65.1 |
| Comparative Example 1 | — | 220 | 2/1 | 4 | 60.3 |

*at the initiation of reaction

It is to be noted that the rate of conversion of formaldehyde di-n-butyl acetal is more than 99% in all cases. In addition to butyl cellosolve, 25 to 35% of by-products [$n-BuOCH_3$, $n-BuOCH_2CH_2OCH_2CH_2OH$, and $n-BuOCH_2CH(O-n-Bu)CH_2OH$] are also produced.

EXAMPLE 8

A reactor is charged with 0.1 mole of acetaldehyde diethyl acetal [$CH_3CH(OEt)_2$], 2 mmoles of dicobalt octacarbonyl [$Co_2(CO)_8$], 2 mmoles of bis(diphenyl phosphino)ethane [$Ph_2PCH_2CH_2PPh_2$], and 30 ml of toluene. Carbon monoxide under pressure is added to the reactor until a pressure of 55 kg/cm² gauge is reached. The temperature is then raised to 160° C and, as a result, the pressure increases to 80 kg/cm² gauge. Hydrogen is added until a total pressure of 240 kg/cm² gauge is obtained. The reaction is continued for 6 hours di-n-butyl acetal [$CH_2(O-n-Bu)_2$], 2.0 mmoles of dicobalt octacarbonyl [$Co_2(CO)_8$], 0.796 g (2.0 mmoles) of bis(diphenyl phosphino)ethane [$Ph_2PCH_2CH_2PPh_2$], and 30 ml of diphenyl ether. The atmosphere in the reactor is replaced with argon and carbon monoxide under pressure until a pressure of 56 kg/cm² guage is reached. The temperature is then increased to 160° C and, as a result, the pressure increases to 80 kg/cm² gauge. Hydrogen is added under pressure until a total pressure of 240 kg/cm² gauge is reached. The reaction is continued for 5 hours until there is no further absorption of gas. After completion of the reaction, the reaction mixture including butyl cellosolve is analyzed by gas chromatography. Analysis shows the yield of butyl cellosolve to be 67%.

The reaction mixture is distilled under reduced pressure in a nitrogen atmosphere. Butyl cellosolve is completely distilled out at a temperature of 120° C and a reduced pressure of 5 mmHg. A dark brown solution of the catalyst dissolved in diphenyl ether is left in the distillation kettle. An additional amount of diphenyl ether is added to this residual solution to prepare 30 ml of a catalyst solution, which is returned to the reaction system. The above-identified reaction procedure is repeated using this recovered catalyst solution.

In a similar manner, the reaction is repeated successively, each time using the catalyst solution recovered from the preceding run. The yields of butyl cellosolve in repeated runs are shown in Table 2.

COMPARATIVE EXAMPLE 3

Example 11 is repeated except that bis(diphenyl phosphino)ethane is not added. The reaction product is subjected to distillation. It has been found that dicobalt octacarbonyl is completely decomposed to a metallic state and separated as a precipitate from the diphenyl ether phase which is colorless and transparent. The yield of butyl cellosolve is also shown in Table 2.

Table 2

|  | Number of recycles | Yield of n-BuOCH$_2$CH$_2$OH (%) |
|---|---|---|
| Example 11 | 0 | 67 |
|  | 1 | 61 |
|  | 2 | 57 |
|  | 3 | 56 |
| Comparative Example 3 | 0 | 48 |

EXAMPLE 12

A reactor is charged with 16 g (0.1 mole) of formaldehyde di-n-butyl acetal [CH$_2$(O—n—Bu)$_2$], 0.341 g (1.0 mmole) of dicobalt octacarbonyl [Co$_2$(CO)$_8$], 0.860 g (2.0 mmoles) of bis(diphenyl phosphino)ethane dioxide [Ph$_2$P(O)CH$_2$CH$_2$P(O)Ph$_2$], and 33 ml of toluene. After the atmosphere in the reactor is replaced with argon, carbon monoxide is added under pressure until a pressure of 54 kg/cm$^2$ gauge at room temperature is reached. The temperature is then raised to 160° C and as a result, the pressure increases to 75 kg/cm$^2$ gauge. Hydrogen is then added under pressure until a total pressure of 225 kg/cm$^2$ gauge is reached. The reaction is continued for 4 hours until there is no absorption of gas. After cooling, the reaction mixture is analyzed by gas chromatography. The result is shown in Table 3.

EXAMPLE 13

Example 12 is repeated except that the amount of dicobalt octacarbonyl is increased to 2.0 mmoles and 0.232 g (2.0 mmoles) of tetramethyl ethylenediamine [Me$_2$NCH$_2$CH$_2$NMe$_2$] is used as the ligand. The result is shown in Table 3.

COMPARATIVE EXAMPLE 4

Example 12 is repeated except that the amount of dicobalt octacarbonyl is increased to 2.0 mmoles and no chelate ligand is added. The result is shown in Table 3.

Table 3

|  | Bidentate chelate ligand (2 mmoles) | Reaction time (hr) | Yield of butyl cellosolve* (%) |
|---|---|---|---|
| Example 12 | Ph$_2$P(O)CH$_2$CH$_2$P(O)Ph$_2$ | 4 | 66 |
| Example 13 | Me$_2$NCH$_2$CH$_2$NMe$_2$ | 5 | 65 |
| Comparative Example 4 | — | 4 | 60 |

*on the basis of CH$_2$(O-n-Bu)$_2$, rate of reaction is more than 99%.

What is claimed is:

1. A process for producing a glycol monoether which comprises reacting
    A. at least one member selected from the group consisting of
        i. an acetal having the general formula:

R$^1$OCHR$^3$OR$^2$ wherein R$^1$ and R$^2$ are the same or different and represent an aliphatic or alicyclic radical of 1 to 8 carbon atoms, or aromatic hydrocarbon radicals of 6 to 7 carbon atoms. R$^3$ represents hydrogen, an aliphatic or alicyclic radical of 1 to 8 carbon atoms or aromatic hydrocarbons radicals of 6 to 7 carbon atoms and the hydrocarbon radicals may have a substituent inert to the reaction,
        ii.
            a. an aldehyde having the general formula:

R$^3$CHO wherein R$^3$ is the same as defined above and
            b. an alcohol having the general formula:

R$^4$OH wherein R$^4$ is the same as R$^1$ or R$^2$, and
        iii.
            c. paraformaldehyde or trioxane and
            d. an alcohol as defined above (b), with
    B. carbon monoxide and
    C. hydrogen
wherein the molar ratio of hydrogen/carbon monoxide is 0.1 to 10, in the presence of
    D. a catalyst comprising
        1. a cobalt compound selected from the group consisting of cobalt carbonyl, cobalt oxide, organic acid salts of cobalt and inorganic acid salts of cobalt, and
        2. at least one compound selected from the group consisting of
            e. trivalent organic phosphorus compounds selected from the group consisting of tertiary phosphines having an alkyl group of 1 to 8 carbon atoms, an aryl group of 6 to 7 carbon atoms or a cyclohexyl group, phosphines having two phosphorus atoms and tertiary phosphites corresponding to the above-mentioned phosphines,
            f. nitrogen-containing bidentate chelate ligand selected from the group consisting of

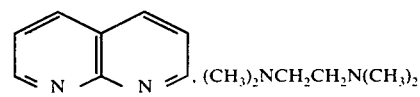

-continued

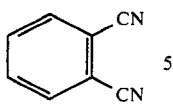

and dinitriles having the general formula: NC(CH$_2$)$_n$CN, wherein n is an integer of 1 to 10, and g. oxygen-containing bidentate chelate ligand selected from the group consisting of CH$_3$COCH$_2$COCH$_3$, CH$_3$CH$_2$ OCOCH$_2$COOCH$_2$CH$_3$ and

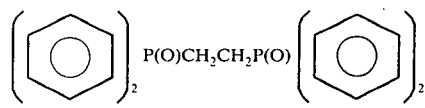

at a temperature of 50° to 300° C and under the pressure of 10 to 1,000 kg/cm$^2$ gauge.

2. A process according to claim 1, wherein the acetal is a formaldehyde dialkyl acetal.

3. A process according to claim 2, wherein the formaldehyde dialkyl acetal is selected from the group consisting of formaldehyde dimethyl acetal and formaldehyde dibutyl acetal.

4. A process according to claim 1, wherein the acetal is an acetaldehyde dialkyl acetal.

5. A process according to claim 4, wherein the acetaldehyde dialkyl acetal is acetaldehyde diethyl acetal.

6. A process according to claim 1, wherein the aldehyde is selected from the group consisting of formaldehyde and acetaldehyde and the alcohol is a saturated aliphatic alcohol having 1 to 8 carbon atoms.

7. A process according to claim 1, wherein the catalyst comprises (1) a cobalt compound selected from the group consisting of cobalt carbonyl, cobalt oxide, organic acid salts of cobalt and inorganic acid salts of cobalt and (2) trivalent organic phosphorus compound selected from the group consisting of tertiary phosphines having an alkyl group of 1 to 8 carbon atoms, an aryl group of 6 to 7 carbon atoms or a cyclohexyl group and phosphines having two phosphorus atoms.

8. A process according to claim 1, wherein the catalyst comprises (1) a cobalt compound selected from the group consisting of cobalt carbonyl, cobalt oxide, organic acid salts of cobalt and inorganic acid salts of cobalt and (2) nitrogen-containing bidentate chelate ligand selected from the group consisting of

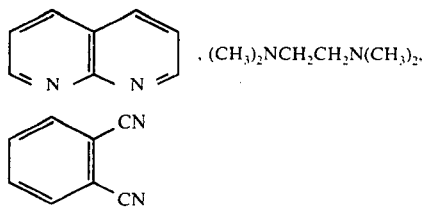

and dinitriles having the general formula: NC(CH$_2$)$_n$CN, wherein n is an integer of 1 to 10.

9. A process according to claim 1, wherein the catalyst comprises (1) a cobalt compound selected from the group consisting of cobalt carbonyl, cobalt oxide, organic acid salts of cobalt and inorganic acid salts of cobalt and (2) oxygen-containing bidentate chelate ligand selected from the group consisting of CH$_3$COCH$_2$COCH$_3$, CH$_3$CH$_2$ OCOCH$_2$COOCH$_2$CH$_3$ and

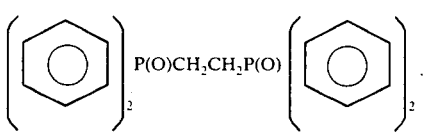

10. A process according to claim 1, wherein the cobalt compound is cobalt carbonyl.

11. A process according to claim 1, wherein the cobalt compound is an organic acid salt selected from the group consisting of cobalt acetate and cobalt laurate.

12. A process according to claim 1, wherein the cobalt compound is an inorganic acid salt of cobalt selected from the group consisting of cobalt nitrate, cobalt sulfate and cobalt halides.

13. A process according to claim 1, wherein the trivalent organic phosphorus compound is a phosphine having two phosphorus atoms selected from the group consisting of bis(diphenylphosphino)methane, bis(diphenylphosphino)ethane and bis(diphenylphosphino)propane.

14. A process according to claim 1, wherein the trivalent organic phosphorus compound is a tertiary phosphine selected from the group consisting of tributylphosphine, trioctylphosphine, triisopropylphosphine, triphenylphosphine, tritolylphosphine and tricyclohexylphosphine.

15. A process according to claim 1, wherein the organic phosphorus compound is a tertiary phosphite selected from the group consisting of tributylphosphite and triphenylphosphite.

16. A process according to claim 1, wherein the reaction is carried out in the presence of a solvent selected from the group consisting of ethers, esters, ketones, aromatic hydrocarbons, aliphatic hydrocarbons and alcohols.

17. A process according to claim 1, wherein the cobalt compound and the trivalent organic phosphorus compound are present in amounts such that the atomic ratio of phosphorus to cobalt is 0.1 to 100.

18. A process according to claim 1, wherein the ratio of a number of gram moles of the bidentate chelate ligand per gram atom cobalt is 0.1 to 100.

19. A process according to claim 1, wherein the reaction mixture is distilled and the distillation residue containing said catalyst is recovered and recycled into said reaction.

* * * * *